US006882745B2

(12) United States Patent
Brankner et al.

(10) Patent No.: US 6,882,745 B2
(45) Date of Patent: Apr. 19, 2005

(54) METHOD AND APPARATUS FOR TRANSLATING DETECTED WAFER DEFECT COORDINATES TO RETICLE COORDINATES USING CAD DATA

(75) Inventors: Keith Brankner, Austin, TX (US); David M. Schraub, Bastrop, TX (US)

(73) Assignee: Freescale Semiconductor, Inc., Austin, TX (US)

( * ) Notice: Subject to any disclaimer, the term of this patent is extended or adjusted under 35 U.S.C. 154(b) by 0 days.

(21) Appl. No.: 10/324,261

(22) Filed: Dec. 19, 2002

(65) Prior Publication Data

US 2004/0121496 A1 Jun. 24, 2004

(51) Int. Cl.$^7$ .............................................. G06K 9/00
(52) U.S. Cl. ...................................... 382/144; 250/307
(58) Field of Search ........................... 250/307; 382/144

(56) References Cited

U.S. PATENT DOCUMENTS

| | | | |
|---|---|---|---|
| 5,401,972 A | 3/1995 | Talbot et al. | 250/491.1 |
| 5,541,411 A | 7/1996 | Lindquist et al. | 250/309 |
| 6,330,053 B1 | 12/2001 | Takayama | 355/77 |
| 6,635,872 B1 * | 10/2003 | Davidson | 250/307 |
| 6,654,489 B1 * | 11/2003 | Wiley et al. | 382/144 |

FOREIGN PATENT DOCUMENTS

EP     1061360     12/2000

OTHER PUBLICATIONS

Baker and Matthews, "Equivalence and efficiency of image alignment algorithms," *Proceedings of the 2001 IEEE Conference on Computer Vision and Pattern Recognition*, 2001.
Jepson et al., "Robust online appearance models for visual tracking," *IEEE Conference on Computer Vision and Pattern Recognition*, 1:415–422, 2001.

* cited by examiner

Primary Examiner—John F. Niebling
Assistant Examiner—Andre' Stevenson
(74) Attorney, Agent, or Firm—Fulbright & Jaworski LLP

(57) ABSTRACT

Systems and methods are described for translating detected wafer defect coordinates to reticle coordinates using CAD data. A wafer inspection image is provided and coordinates of potential defects in the wafer are determined. Then the wafer inspection image is converted into a predetermined image format. CAD data for the device under test is then used to produce a second image, also in the predetermined image format. The CAD-derived image and the wafer-derived image are then aligned, and the coordinates of potential defects in the wafer are converted into CAD coordinates. The CAD coordinates are then used to navigate through the reticle for the wafer in order to locate reticle defects corresponding to the detected wafer defects.

15 Claims, 4 Drawing Sheets

METHOD AND APPARATUS FOR TRANSLATING DETECTED WAFER DEFECT COORDINATES TO RETICLE COORDINATES USING CAD DATA

BACKGROUND OF THE INVENTION

1. Field of the Invention

The invention relates generally to the field of semiconductor manufacturing. More particularly, the invention relates to semiconductor inspection and measurement.

2. Discussion of the Related Art

Inspection and measurement are important areas of semiconductor manufacturing. Measurement may be defined as the ability to precisely quantify physical, dimensional, or electrical properties of different materials. Numerous measurement tools are routinely used to monitor the quality of semiconductor manufacturing processes. Inspection relates to the ability to observe and quantify defects, and inspection tools include a variety of optical instruments used for these purposes. In sub-micron applications, inspection equipment such as scanning electrical microscopes (SEMs) are widely used.

As geometries get smaller, the ability to observe defects in wafers and reticles (masks) becomes more challenging and expensive. Existing wafer and reticle inspection tools find defects which can only be disposed when their location is understood. Typically, engineers spend many hours or days attempting to determine the location of defects in order to be able to classify and judge their impact on production yield. Consequently, defects are often disposed without regard to their location but rather only to its size.

Thus, there is a need for a method and apparatus for defect location, minimizing engineering defect reduction efforts, and improving the forecast of measures such as production yield.

SUMMARY OF THE INVENTION

There is a need for the following embodiments. Of course, the invention is not limited to these embodiments.

In accordance with one embodiment of the invention, defects in a device under test are located using CAD data for the device under test. An inspection image is provided of a device under test and coordinates of potential defects in the device under test are determined. Then the inspection image is converted into a predetermined image format. CAD data for the device under test is then used to produce a second image, also in the predetermined image format. The CAD-derived image and the device-derived image are then aligned, and the coordinates of potential defects in the wafer are converted into CAD coordinates. The CAD coordinates are then used to navigate through the reticle for the wafer in order to located reticle defects corresponding to the detected wafer defects.

According to another aspect of the invention, an apparatus includes a stage for holding a wafer under test, an image and defect detection device coupled to the stage for producing an inspection image of the wafer under test and for producing stage coordinates of defects detected in the wafer under test, CAD data for the wafer under test, a control unit coupled to control the stage and the image and defect detection device, and a synchronization unit coupled to the control unit and to the image and defect detection device, for converting stage coordinates of defects in the wafer under test into wafer reticle coordinates as a function of both the inspection image of the wafer under test and the CAD data.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore nonlimiting, embodiments illustrated in the drawings, wherein like reference numerals (if they occur in more than one view) designate the same or similar elements. The invention may be better understood by reference to one or more of these drawings in combination with the description presented herein. It should be noted that the features illustrated in the drawings are not necessarily drawn to scale.

DETAILED DESCRIPTION

Figure 1:
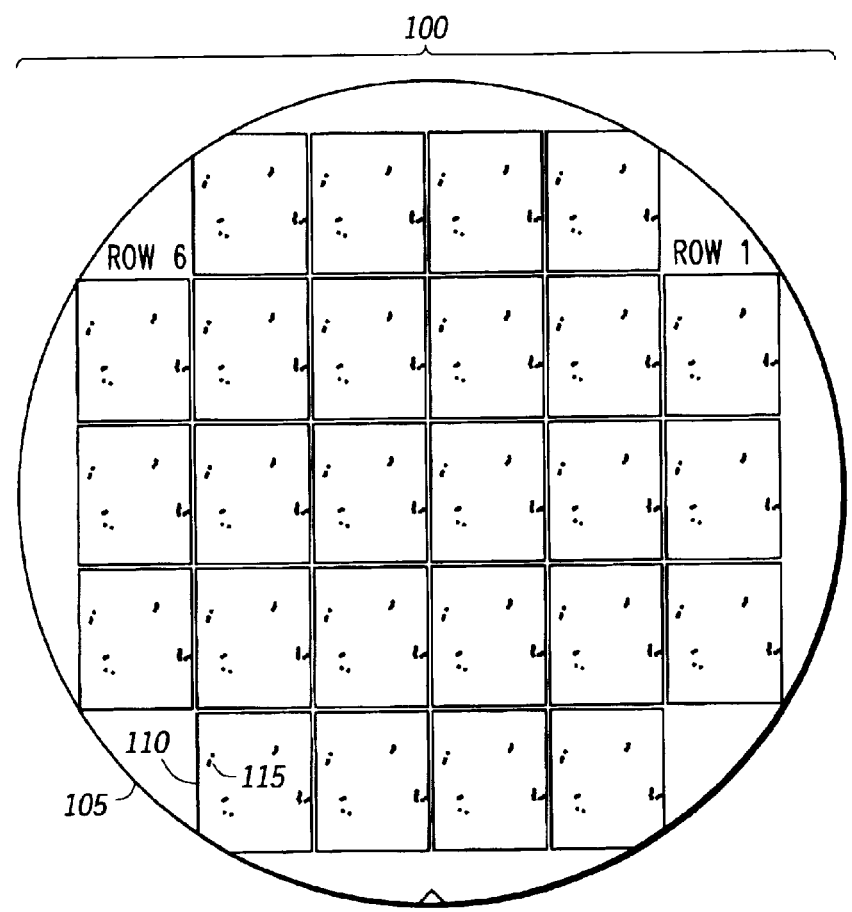
FIG. 1 is an image of a wafer, illustrating an aspect of the invention.

The invention and the various features and advantageous details thereof are explained more fully with reference to the nonlimiting embodiments that are illustrated in the accompanying drawings and detailed in the following description. It should be understood that the detailed description and the specific examples, while indicating specific embodiments of the invention, are given by way of illustration only and not by way of limitation. Various substitutions, modifications, additions and/or rearrangements within the spirit and/or scope of the underlying inventive concept will become apparent to those of ordinary skill in the art from this disclosure.

During inspection of wafers in a fabrication facility, repeater defects or anomalies may show up from time to time. Repeater defects are defects that are repeated in each reticle field of a wafer, and may be due to, for example, problems with the reticle mask or plate. When wafer defects are repeated from one reticle field to another, an inspection tool may flag such defects and store them in a defect file. The defect file contains the stage X-Y coordinates for each potential detected defect. Using the defect file in a review station, a review tool may be driven to the locations found in the wafer or die for that particular defect or missing feature. Unfortunately, the locations of the repeater in the defect file may be off by as much as approximately 5 to 15 microns from one repeater defect to another in a different reticle field. This offset may be due to, for example, stage inconsistencies from tool to tool or mechanical tolerances, making it difficult to translate defect positions between the wafer and the reticle mask.

The present invention may include a method and/or apparatus for determining the absolute X-Y location of semiconductor features or the like by using a computer-aided design (CAD) layout overlaid onto an inspection image. The features may be, for example, a defect or an anomaly. The invention may include tagging the defect or missing feature by appending absolute CAD X-Y coordinates to the defect file.

In one embodiment, the CAD layout and the inspection image may be automatically synchronized. When the stage on the review tool moves across the die, the overlaid CAD image for a particular layer may move in tandem. This automated synchronization method may take both the image seen on the inspection tool screen and the generated CAD image. In another embodiment, an operator may be provided with the inspection image and the overlaid CAD drawing in the same screen. Once the synchronization described above is performed in accordance with the invention, the defect file for a particular wafer with repeater defects may be loaded into the inspection or review tool and driven to the particular defect or missing feature of interest. The defect's absolute CAD X-Y may be recorded in the form of a tagged defect file, or a tagged file.

Typically, reticle plates are four times larger than the device being printed and are a mirror image of the reticle field. In one embodiment, the CAD X-Y coordinates may be transformed accordingly to compensate for differences between the reticle plate and a reticle field. A reticle plate review tool, which is similar in structure to a fabrication inspection tool, can accurately be driven to the correct defect location using the CAD X-Y coordinates. Once the defective area is correctly found on the reticle plate, analysis tools may be used to determine possible problems with that particular feature.

In one embodiment, after repairing the reticle plate, a print test may be performed and the wafer inspection review tools may be returned to the same location in order to determine the output of the repair. Additional defect locations found on the plate at the mask shop may be also reported using the methods described herein, and wafer fabrication inline inspection tools may be driven to those same locations using absolute CAD X-Y coordinates.

Referring to FIG. 1, a wafer 105 is depicted, illustrating an aspect of the invention. In this exemplary embodiment, the wafer 105 may include, for example, six rows 100 of reticle fields 110. Reticle fields 110 are formed in a known manner in an ordered pattern on Wafer 105 using step-and-repeat photolythographic processes. Typically, a reticle field 110 (which may correspond to an individual die) may contain undesirable defects 115. The defects 115 may be chemical or structural irregularities that degrade the crystal structure of silicon or of the deposited materials that reside on the reticle field 110 surface.

Figure 2:
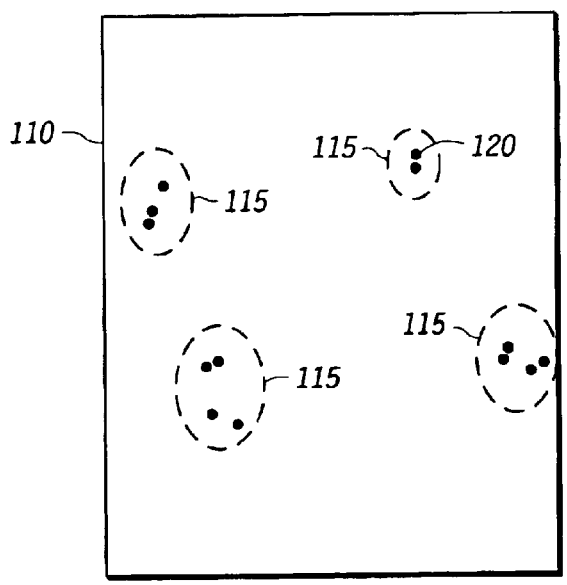
FIG. 2 is an image of a reticle, illustrating an aspect of the invention.

Referring to FIG. 2, an individual reticle field 110 detailed in FIG. 1 is depicted illustrating an aspect of the invention. The reticle field 110 includes defects 115. In this example, one of the defects 115 is a repeater defect 120. The repeater defect 120 may repeat itself throughout some or all of the other reticle fields in wafer 105 detailed in FIG. 1.

If reticle fields 110 of wafer 105 depicted in FIG. 1 were stacked onto a single reticle field shot showing only repeater defects, the spread associated with stage run out caused by the inspection tool would be seen as it scans across and down the wafer.

Figure 3:
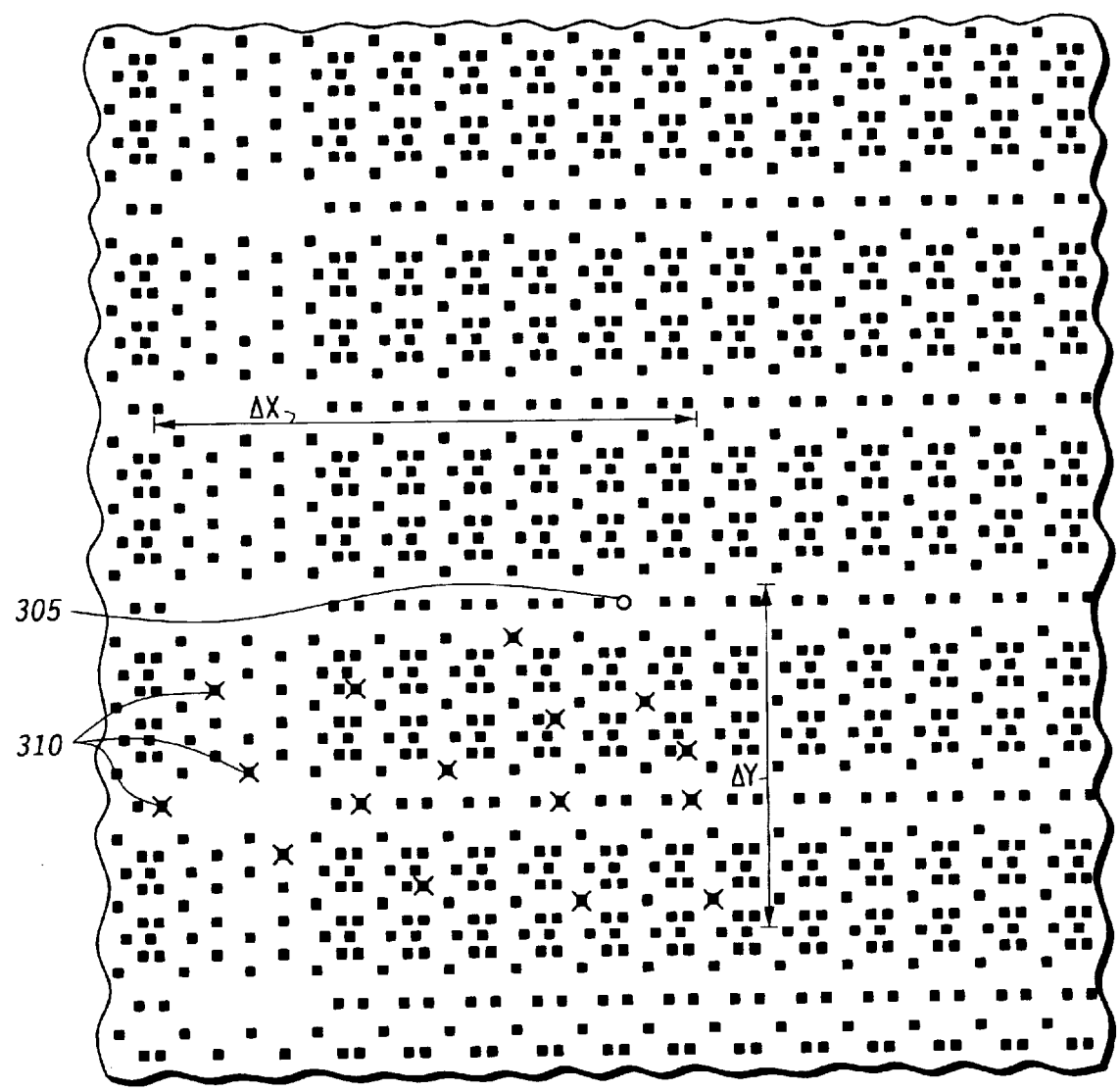
FIG. 3 is an image of a repeater defect spread across different reticle fields, illustrating an embodiment of the invention.

For example, referring to FIG. 3, the repeater defect 120 detailed in FIG. 2 spread across different reticle fields is depicted illustrating one embodiment of the invention. A circle 305 indicates the actual position of the repeater defect 120. A plurality of crossed squares 310 represent a single stack of the same defect in the same portion of different reticle fields located in different parts of the wafer. In one practical embodiment, the stage accuracy as the inspection system scans vertically and horizontally across the wafer may shows a spread of as much as 10 microns in each direction ($\Delta X$ and $\Delta Y$ in FIG. 3). Thus, the same reticle defect that manifests itself in different reticle fields as a repeater defect may be perceived to be spread across an area of about 20 to 100 square microns in different reticle fields. In one embodiment, the invention may include a defect repeater automation method which finds common coordinates of defect locations within the wafer and outputs a tagged defect file populated with the CAD X-Y coordinates of repeater defects, aiding in failure analysis by providing the exact location of particular defects, and improving accuracy in existing reticle automation software.

Figure 4:
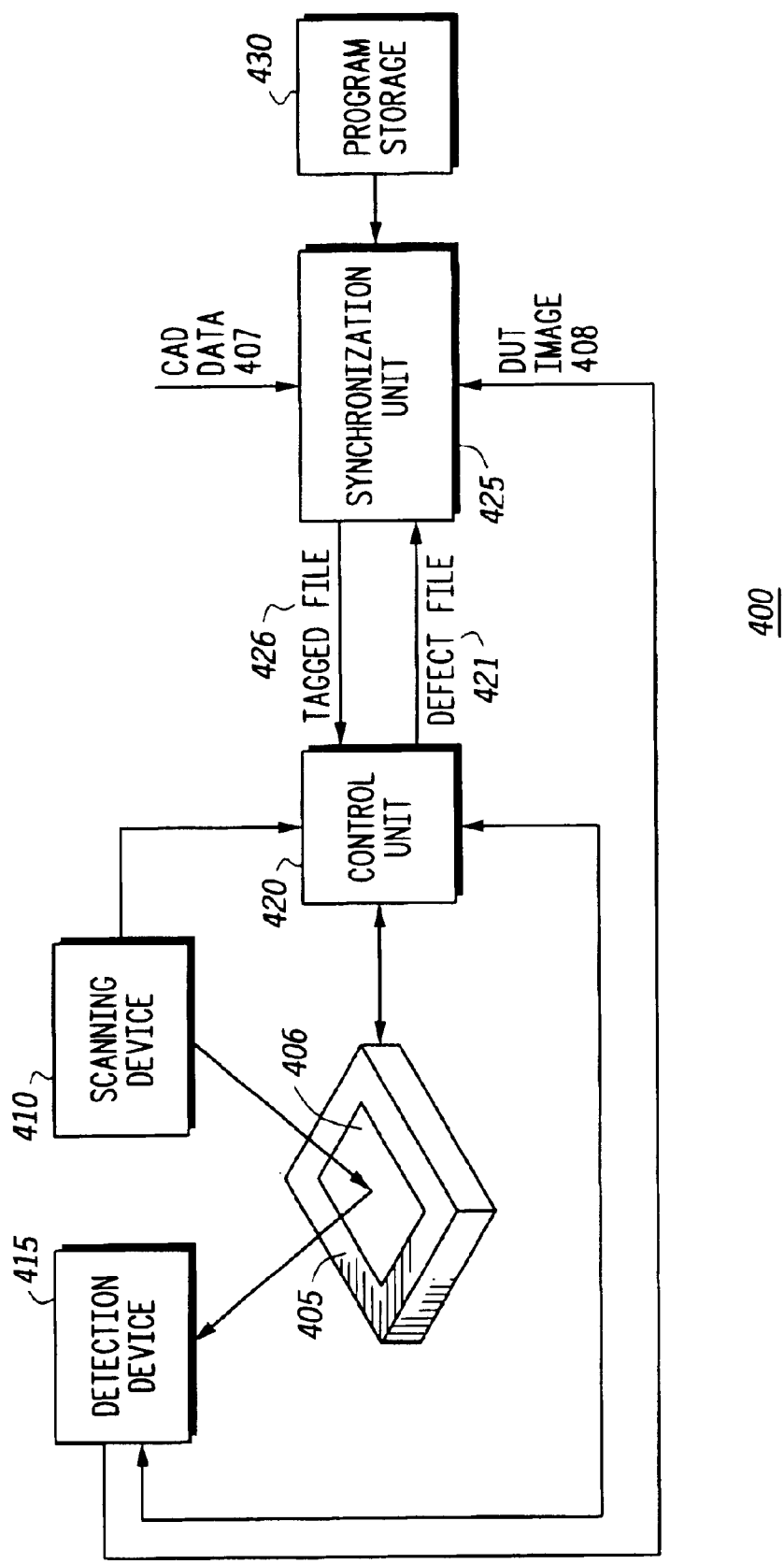
FIG. 4 is a block diagram of a semiconductor inspection apparatus, representing an embodiment of the invention.

Referring to FIG. 4, a block diagram of a semiconductor inspection apparatus 400 is depicted according to an exemplary embodiment of the invention. A stage 405 is coupled to a scanning device 410, and it may include a device under test (DUT) 406. The device under test 406 may be, for example, a wafer. The scanning device 410 may be, for example, a scanning electron microscope (SEM) or an optical device to provide an image of a wafer defect and/or surrounding features to a detection device 415. A control unit 420 may be circuitry or a computer which controls, coordinates, and gathers information from the stage 405, scanning device 410, and detection unit 415. A synchronization unit 425 is coupled to the control unit 420, and a program storage media 430 is coupled to the synchronization unit 425.

The scanning and detection devices 410, 415 may be, for example, a scanning electron microscope (SEM) or an optical based system. The control unit 420 may move the stage 405 in space and control operation of the scanning and detection devices 410, 415. As the stage 405 moves under the inspection system, stage coordinates along with detection and scanning information may be kept track of by the control unit 420. The control unit 420 and the synchronization unit 425 work in conjunction with each other to coordinate wafer and/or intra-die locations for overlaying and synchronizing a CAD generated data 407 onto a captured inspection image 408 generated by the inspection tool (optical or SEM). The inspection image 408 may also be referred to as a DUT inspection image, a captured DUT image, or a wafer image. The control unit 420 may also provide the synchronization unit 425 with a defect file containing stage X-Y coordinates of defects and features.

The synchronization unit 425 processes the CAD data 407 and the inspection image 408. The synchronization unit 425 operates to convert the CAD data 407 into a rendered image in a predetermined image format. The rendered image may be squared off at the ends to better represent the inspection image 408 provided by the inspection tool. Next, an alignment algorithm may be used for synchronizing and compensating for any offsets between the CAD data 407 and the inspection image 408. In one embodiment, the synchronization unit 425 may overlay an image derived from the CAD data 407 onto the inspection image 408, or vice versa. In another embodiment, the synchronization unit 425 may receive the inspection image 408 from the detection device 415 (for example, a wafer image or a reticle image), retrieve the CAD data 407 from a database (not shown), perform a synchronization operation, receive a defect file 421 from the control unit 420, map a CAD feature coordinate to a reticle field defect coordinate, and provide the control unit 420 with tagged defect file 426 containing CAD X-Y coordinates of defects.

In practice, the synchronization unit 425 may be a programmable circuit, such as, for example, a computer, microprocessor or digital signal processor-based (DSP) circuit, that operates in accordance with instructions stored in the program storage media 430. The program storage media 430 may be any type of readable memory including, for example, a magnetic or optical media such as a card, tape or disk, or a semiconductor memory such as a PROM or FLASH memory. The synchronization unit 425 may be implemented in software, such as, for example, a software defined algorithm, or the functions may be implemented by a hardware circuit, or by a combination of hardware and software.

Figure 5:
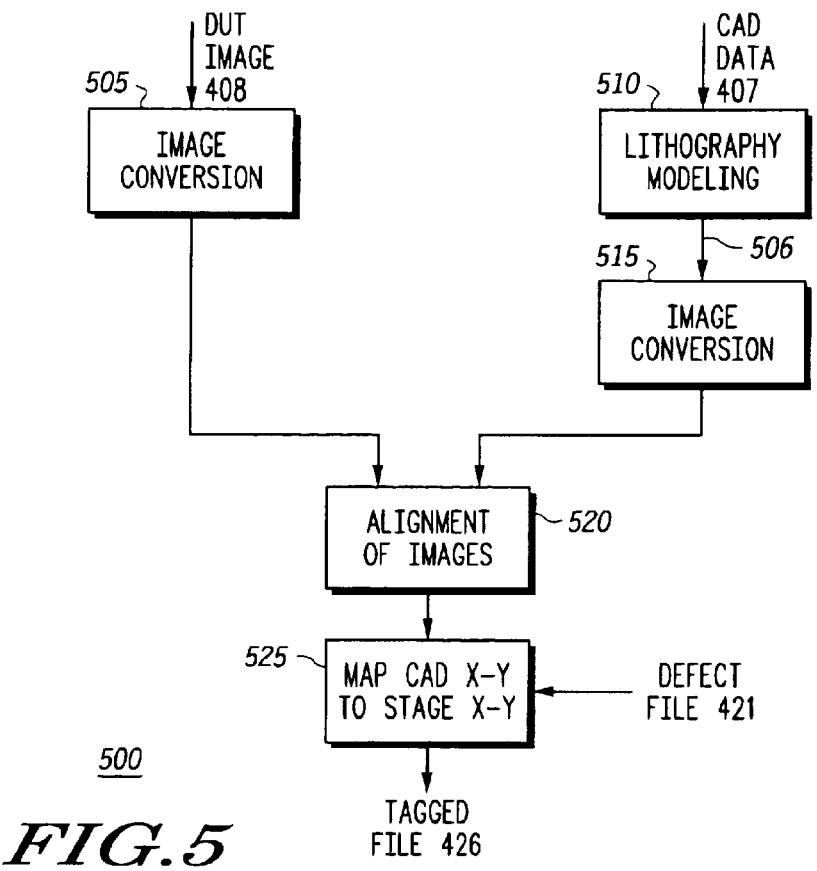
FIG. 5 is a flowchart of a translation method, representing an embodiment of the invention.

When the synchronization unit 425 is a programmable circuit, a program, such as that presented below and discussed in detail with reference to FIG. 5, is stored in the program storage media 430 to create an apparatus in accordance with the present invention that operates in accordance with the methods of the present invention. In the alternative, the synchronization unit 425 may be hard-wired or may use predetermined data tables, or may be a combination of hard-wired and programmable circuitry.

Referring to FIG. 5, a flowchart of translation method 500 is depicted, representing an embodiment of the invention. The method 500 may be stored in the program storage media 430 and performed by the synchronization unit 425, both detailed in FIG. 4. The inspection image 408 is processed by a first image conversion step 505 where a die image is converted from a raster scan or any other image format into a predetermined image format. The CAD image 407 is received from a database (not shown) and is processed by a lithography modeling step 510, producing a rendered die or wafer image 506. In one exemplary embodiment, the lithography modeling method performed by step 510 may use, for example, the Prolith lithography software available from Finle Technology, Inc. The rendered image 506 is further processed by a second image conversion step 515 that converts rendered image 506 into the same predetermined image format as that produced by block 505. The predetermined image format may be any image format such as, for example, a tagged-image file format (TIFF) conversion, a joint photographic experts group image (JPEG), a graphic interchange format image (GIF), a printer description file (PDF), or any other image format.

The outputs of the image conversion steps 505, 515 are processed by an alignment step 520. The alignment of the two images, both in the same predetermined image format and at the same magnification, are matched by all the edge features of the image, yielding a map of inspection image to CAD image coordinates. Step 525 receives the defect file 421 containing stage X-Y coordinates of a defect and appends to it the corresponding CAD X-Y coordinates of the defect, outputting the tagged defect file 426.

The alignment step 520 may use any of a variety of alignments methods. For example, the alignment step 520 may use a gradient descent method, such as an additive algorithm, a compositional algorithm, or an inverse compositional algorithm. While an additive algorithms estimate additive increments to alignment parameters, compositional algorithms estimate incremental warps. Gradient descent algorithms are well known to one of ordinary skill in the art. In one exemplary embodiment, the alignment method performed by step 520 may use, for example, the image alignment method used in the 8250 Series CD SEM tool, which is a critical dimension scanning electron micrograph tool for measuring very small features, made available by KLA-Tencor. In another embodiment, the invention may use the image alignment method used in the KLA-Tencor ES20 tool.

Referring to FIGS. 4 and 5, the invention includes a method and/or apparatus for providing the control unit 420 of a semiconductor inspection apparatus 400 with a map of wafer coordinates to CAD coordinates. The control unit can perform a fine alignment of the stage 405. The synchronization unit 425 may be useful in defect location.

Figure 6:
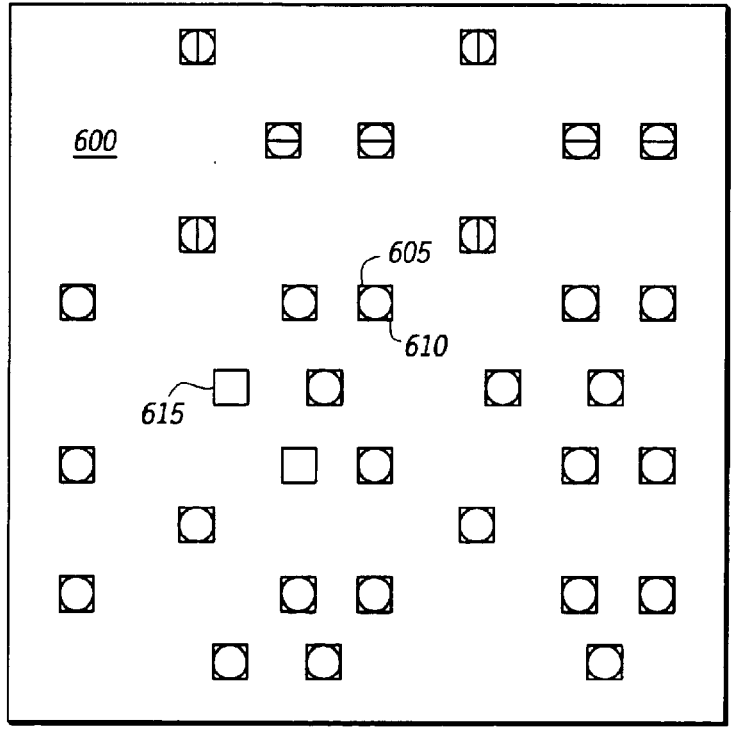
FIG. 6 is a synchronized CAD and wafer image, illustrating an aspect of the invention.

Referring to FIG. 6, a synchronized CAD and wafer image 600 is depicted, illustrating an aspect of the invention. A square 605 represents a CAD element or feature, and a circle 610 represents a wafer element or feature. The overlaying of wafer and CAD images illustrated in FIG. 6 is done by the alignment block 520 detailed in FIG. 5.

In one exemplary embodiment, the invention may be used to detect wafer or reticle defects through CAD navigation. A wafer element 615 found without a corresponding CAD feature indicates a possible wafer defect. For example, the wafer defect may be a missing contact. In another embodiment, the defect detection may be automated. The absolute defect location may be recorded in a defect file or a database.

In one embodiment, the invention may include synchronizing and overlaying a CAD image to a wafer image, automatically locating wafer defects on the resulting overlaid image, and adding absolute CAD X-Y coordinates of the wafer defects to a defect file or database. The invention may also include using the absolute CAD defect coordinates of a defect file or database for driving an inspection system and automatically locating defects in a reticle which correspond to the wafer defects.

The terms a or an, as used herein, are defined as one or more than one. The term plurality, as used herein, is defined as two or more than two. The term another, as used herein, is defined as at least a second or more. The terms including and/or having, as used herein, are defined as comprising (i.e., open language). The term coupled, as used herein, is defined as connected, although not necessarily directly, and not necessarily mechanically. The term program or software, as used herein, is defined as a sequence of instructions designed for execution on a computer system. A program, or computer program, may include a subroutine, a function, a procedure, an object method, an object implementation, an executable application, an applet, a servlet, a source code, an object code, a shared library/dynamic load library and/or other sequence of instructions designed for execution on a computer system.

The appended claims are not to be interpreted as including means-plus-function limitations, unless such a limitation is explicitly recited in a given claim using the phrase(s) "means for" and/or "step for." Subgeneric embodiments of the invention are delineated by the appended independent claims and their equivalents. Specific embodiments of the invention are differentiated by the appended dependent claims and their equivalents.

What is claimed is:

1. A method of locating repeater defects in a device under test, comprising:
   providing an inspection image of a device under test including detected coordinates of potential repeater defects;
   converting the inspection image into a first image in a predetermined image format;
   providing CAD data for the device under test;
   converting the CAD data into a second image in the predetermined image format;
   aligning the first and second images;
   converting the detected coordinates of potential repeater defects into CAD coordinates; and
   locating repeater defects as a function of the CAD coordinates.

2. The method of claim 1, the device under test comprising a wafer.

3. The method of claim 1, the device under test comprising a die of a wafer.

4. The method of claim 1, further comprising, locating repeater defects in a reticle for the device under test, as a function of the CAD coordinates.

5. The method of claim 1, the step of converting the CAD data into the second image comprising, performing a lithography modeling step.

6. The method of claim 1, the detected coordinates of potential repeater defects comprising a repeater defect file.

7. The method of claim 6, the step of converting the detected coordinates into CAD coordinates comprising, mapping the repeater defect file to CAD coordinates to produce a tagged data file.

8. The method of claim 7, the repeater defect file comprising wafer stage coordinates.

9. A method for locating repeater defects in a semiconductor wafer reticle, comprising:
   generating a wafer image of a semiconductor wafer under test;
   determining stage coordinates for detected potential repeater defects in the wafer under test;
   generating a CAD image from CAD data related to the semiconductor wafer under test;
   aligning the wafer image and the CAD image and determining CAD coordinates from the stage coordinates corresponding to said potential repeater defects; and
   locating repeater defects in a semiconductor wafer reticle for the semiconductor wafer under test as a function of the CAD coordinates.

10. The method of claim 9, the step of generating a CAD image comprising, conditioning said CAD data using lithography modeling.

11. The method of claim 9 further comprising, storing CAD coordinates corresponding to said potential repeater defects in a repeater defect file.

12. The method of claim 11 further comprising, mapping the repeater defect file to CAD coordinates to produce a tagged data file.

13. A method of locating repeater defects in a device under test, comprising:
   mounting a device under test on a stage;
   generating an image of the device under test;
   determining stage coordinates for detected potential repeater defects in the device under test;
   generating a CAD image from CAD data corresponding to the device under test;
   converting the image of the device under test and the CAD image into a common image format;
   aligning the image of the device under test and the CAD image in the common image format;
   determining CAD coordinates of the potential repeater defects from the stage coordinates for the detected potential repeater defects; and
   locating repeater defects as a function of the CAD coordinates.

14. The method of claim 13, the device under test comprising a wafer.

15. The method of claim 14 further comprising, locating repeater defects in a reticle of the wafer as a function of the CAD coordinates.

* * * * *